United States Patent
Utsumi et al.

(10) Patent No.: US 8,513,417 B2
(45) Date of Patent: Aug. 20, 2013

(54) METHOD FOR SYNTHESIS OF NITROXYL RADICAL

(75) Inventors: Hideo Utsumi, Fukuoka (JP); Kiyoshi Sakai, Fukuoka (JP); Kenichi Yamada, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 515 days.

(21) Appl. No.: 12/523,341

(22) PCT Filed: Jan. 30, 2008

(86) PCT No.: PCT/JP2008/051899
§ 371 (c)(1),
(2), (4) Date: Jul. 16, 2009

(87) PCT Pub. No.: WO2008/093881
PCT Pub. Date: Aug. 7, 2008

(65) Prior Publication Data
US 2010/0076190 A1 Mar. 25, 2010

(51) Int. Cl.
*C07D 221/20* (2006.01)
(52) U.S. Cl.
USPC .................................. 546/16; 546/17; 546/18
(58) Field of Classification Search
USPC .................................. 546/16, 17, 18
See application file for complete search history.

(56) References Cited

FOREIGN PATENT DOCUMENTS

| JP | 44-12414 | 6/1969 |
| JP | 46-31733 | 9/1971 |
| JP | 47-1627 | 1/1972 |
| JP | 50-10281 | 4/1975 |

OTHER PUBLICATIONS

Miura, Y., et al. "Living radical polymerization of styrene mediated by spiro ring-substituted piperidinyl-N-oxyl radicals. The effect of the spiro rings on the control of polymerization." *Polymer* (2003) vol. 44, No. 18, pp. 5187-5194.
Yoshioka, T., et al. "Studies on stable free radicals. VIII. The synthesis and oxidation of hindered 4-oxopiperidine derivatives." *Bulletin of the Chemical Society of Japan* (1972) vol. 45. No. 2, pp. 636-638.
Miura, Y., et al. "Low-Temperature "Living" Radical Polymerization of Styrene in the Presence of Nitroxides with Spiro Structures." *Macromolecules* (2001) vol. 34, No. 3, pp. 447-455.
Wilen, C. E., et al., "Synthesis of Novel Hindered Amine Light Stabilizers (HALS) and Their Copolymerization with Ethylene or Propylene over Both Soluble and Supported Metallocene Catalyst Systems." *Macromolecules* (2000) vol. 33, No. 14, pp. 5011-5026.
Ma, Z., et al. Oxoammonium salts. 5. A new synthesis of hindered piperidines leading to unsymmetrical TEMPO-type nitroxides. Synthesis and enantioselective oxidations with chiral nitroxides and chiral oxoammonium salts. *J. Org. Chem.* (1993) vol. 58, No. 18, pp. 4837-4843.
Wetter, C., et al. "Steric and electronic effects in cyclic alkoxyamines—Synthesis and applications as regulators for controlled/living radical polymerization." *Chemistry—European Journal* (2004) vol. 10, No. 5, pp. 1156-1166.
Jockusch, S., et al. "Time Resolved CW-EPR Spectroscopy of Powdered Samples: Electron Spin Polarization of a Nitroxyl Radical Adsorbed on NaY Zeolite, Generated by the Quenching of Excited Triple Ketones.." *J. Phys. Chem B* (2001) vol. 105, No. 31, pp. 7477-7481.
Utsumi, H., et al. "Simultaneous molecular imaging of redox reactions monitored by Overhauser-enhanced MRI with $^{14}$N- and $^{15}$N-labeled nitroxyl radicals." *PNAS* (2006) vol. 103, No. 5, pp. 1463-1468.
Molawi, K., et al. "Tin-Free Radical Alkoxyamine Addition and Isomerization Reactions by Using the Persistent Radical Effect: Variation of the Alkoxyamine Structure." *Chem. Eur. J.* (2005) vol. 11, pp. 2335-2350.
Studer, A., et al. "Nitroxide-Mediated Radical Processes." *The Chemical Record* (2005) vol. 5 pp. 27-35.
Wienhofer, I. C.,et al. "Microflow Radical Carboaminoxylations with a Novel Alkoxyamine." *Organic Letters* (2009) vol. 11, No. 11, pp. 2457-2460.
Kinoshita, Y., et al. "Development of novel nitroxyl radicals for controlling reactivity with ascorbic acid." *Free Radical Research* (2009) vol. 43 (6), pp. 565-571.
Partial English translation of JP 50-10281 dated Apr. 19, 1975.
Partial English translation of JP 47-1627 dated Jan. 17, 1972.
Partial English translation of JP 44-12414 dated Jun. 5, 1969.
Partial English translation of JP 46-31733 dated Sep. 16, 1971.

*Primary Examiner* — Rita Desai
(74) *Attorney, Agent, or Firm* — Ladas & Parry LLP

(57) ABSTRACT

The problem to be solved by the present invention is to provide a highly-versatile method for producing a nitroxyl radical derivative, in which position-2 and position-6 in a TEMPO-based compound can be easily substituted, and further, a method for producing a nitroxyl radical derivative, in which a nitrogen nucleus is labeled with $^{15}$N. The above-described problem can be solved by reacting a triacetoneamine derivative with ketone or aldehyde in the presence of ammonium salt or a $^{15}$N-labeled compound thereof to obtain a 2,6-substituted-4-piperidone derivative.

6 Claims, 1 Drawing Sheet

METHOD FOR SYNTHESIS OF NITROXYL RADICAL

TECHNICAL FIELD

The present invention relates to a method for producing a nitroxyl radical derivative, in particular, a nitroxyl radical derivative having substituents at position-2 and position-6 in a TEMPO-based compound.

BACKGROUND ART

Nitroxyl radical is a substance having an unpaired electron, and because of a variety of properties thereof, it is widely used as an antioxidative substance, a chemical cell, a polymerization agent or the like. In addition, nitroxyl radical is highly sensitive to a free radical such as active oxygen, and the distribution of nitroxyl radical in vivo varies depending on the basic structure thereof and the type of substituent. Therefore, utilizing these natures, nitroxyl radical can also be used as a contrast agent for following a free radical reaction in vivo. The present inventors focused their attention on this point and already indicated that novel image analysis can be carried out in vivo by utilizing the simultaneous separate imaging method using $^{14}N$-labeled and $^{15}N$-labeled compounds (see H. Utsumi, K. Yamada, K. Ichikawa, K. Sakai, Y Kinoshita, S. Matsumoto and M. Nagai, PNAS, 103, 1463 (2006)).

Conventionally, nitroxyl radical is generally synthesized from acetone, ammonia (or ammonia chloride), etc. Typical examples of nitroxyl radicals obtained using this technique include 2,2,6,6-tetramethylpiperidine-N-oxyl (TEMPO) derivatives and 2,2,5,5-tetramethylpyrrolidine-N-oxyl (PROXYL) derivatives.

Reactivities of these conventional nitroxyl radicals to a free radical significantly differ from each other depending on the difference of skeleton (TEMPO-based or PROXYL-based). However, reactivities of TEMPO-based compounds do not differ from each other so much. It is thought that this is because structures around the unpaired electron in nitroxyl radical, i.e., substituents at position-2 and position-6 are not substituted with other substituents.

Several research groups have attempted to carry out replacement of substituents at position-2 and position-6 in a TEMPO-based compound. For example, Miura et al. succeeded in synthesis of 2,6-dispirocyclohexane-4-piperidone using ammonia as a starting material and acetonine as an intermediate (see Y. Miura, N. Nakamura and I. Taniguchi, Macromolecules, 34, 447 (2001)). Wetter et al. succeeded in synthesis of 2,2,6,6-tetraethyl-4-oxo-TEMPO using bisphosphonate as a starting material (see C. Wetter, J. Gierlich, C. A. Knoop, C. Müller, T. Schulte and A. Studer, Chem. Eur. J., 10, 1156 (2004)).

However, these synthesis methods have the following problems: the stability of an intermediate compound such as acetonine is low; many steps for synthesis are required; and there is a lack of application to synthesis of other compounds; etc.

DISCLOSURE OF THE INVENTION

Under the above-described circumstances, a highly-versatile method for producing a nitroxyl radical derivative, in which substituents can be introduced into position-2 and position-6 in a TEMPO-based compound using a simple method, and further, a method for producing a nitroxyl radical derivative, in which a nitrogen nucleus is labeled with $^{15}N$, are desired.

The present inventors diligently made researches in order to solve the above-described problems, and found that substituents can be easily introduced into position-2 and position-6 in a triacetoneamine derivative by reacting the triacetoneamine derivative as a starting material with ketone or aldehyde in the presence of ammonium salt. The present inventors further found that, by oxidizing this compound using an oxidant such as hydrogen peroxide, a nitroxyl radical derivative having substituents at position-2 and position-6 can be obtained in a high yield. In addition, the present inventors found that, by utilizing ammonium salt in which a nitrogen nucleus is labeled with $^{15}N$ in the above-described reaction, a compound in which a nitrogen nucleus of a product is labeled can be obtained. Thus, the present invention was achieved.

That is, the present invention provides a method for producing a 2,6-substituted-4-piperidone derivative, a method for producing a nitroxyl radical derivative using a compound obtained using the method, a compound obtained using the above-described methods, etc., as described below:

[1] A method for producing a 2,6-substituted-4-piperidone derivative represented by the following formula:

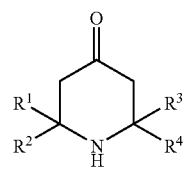

(I)

[wherein in the formula: $R^1$, $R^2$, $R^3$ and $R^4$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^1$, $R^2$, $R^3$ and $R^4$ is a group other than a hydrogen atom; and $R^1$ and $R^2$ and/or $R^3$ and $R^4$ may be independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom],
wherein the method comprises the step of reacting a triacetoneamine derivative represented by the following formula:

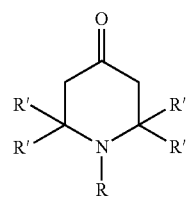

(1)

[wherein in the formula: R is a hydrogen atom or a $C_1$-$C_6$ alkyl group; and R's are each independently a $C_1$-$C_6$ alkyl group],
(in which the case where the triacetoneamine derivative represented by the formula (1) is completely identical to the 2,6-substituted-4-piperidone derivative represented by the formula (1) is excluded), with a ketone or aldehyde derivative represented by the following formula:

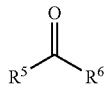
(2)

[wherein in the formula: $R^5$ and $R^6$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^5$ and $R^6$ is a group other than a hydrogen atom; and $R^5$ and $R^6$ may be crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom], in the presence of ammonium salt.

[2] The production method according to item [1], wherein in the formula (1), R is a methyl group.

[3] The production method according to item [1] or [2], wherein the 2,6-substituted-4-piperidone represented by the formula (1) and the ammonium salt are $^{15}$N-labeled compounds.

[4] A 2,6-substituted-4-piperidone derivative, which is obtained using the method according to any one of items [1] to [3].

[5] A 2,6-substituted-4-piperidone derivative represented by the following formula:

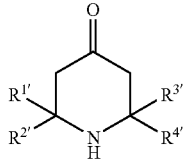
(I')

[wherein in the formula: $R^{1'}$, $R^{2'}$, $R^{3'}$ and $R^{4'}$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^{1'}$, $R^{2'}$, $R^{3'}$ and $R^{4'}$ is a group other than a hydrogen atom; and $R^{1'}$ and $R^{2'}$ and/or $R^{3'}$ and $R^{4'}$ are independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom (wherein the case where $R^{1'}$ and $R^{2'}$ and/or $R^{3'}$ and $R^{4'}$ form a cyclohexane ring with no substituent is excluded)].

[6] The 2,6-substituted-4-piperidone derivative according to item [5], which is represented by the following formula:

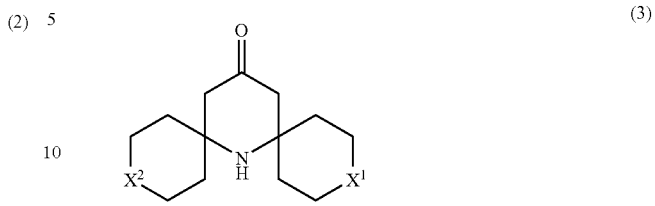
(3)

[wherein in the formula: $X^1$ and $X^2$ are each independently a substituted or unsubstituted $C_4$-$C_{20}$ cycloalkylene group which may be interrupted by an oxygen atom, a nitrogen atom or a sulfur atom; carbonyl group; acetamide group; sulfonyl group; sulfinyl group; an oxygen atom; or a sulfur atom].

[7] A 2,6-substituted-4-piperidone derivative represented by the following formula:

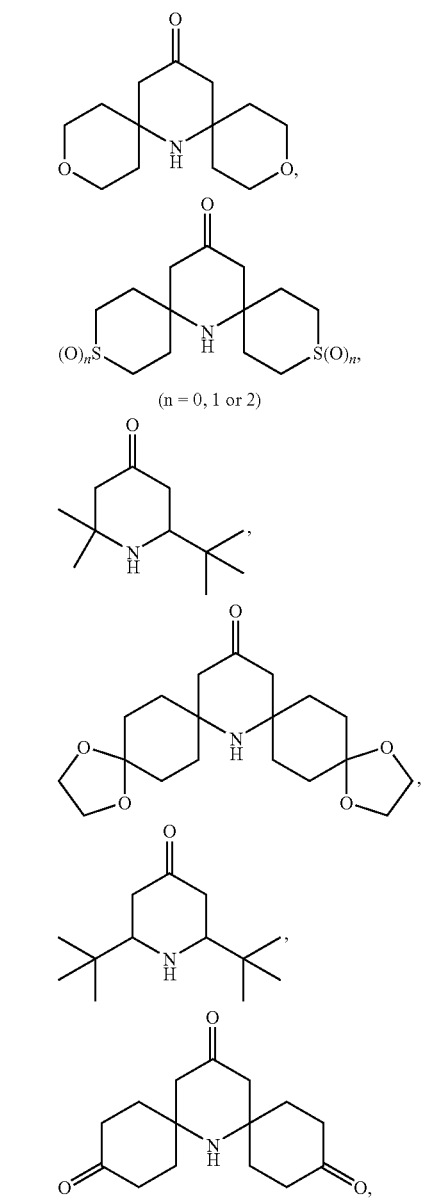

-continued

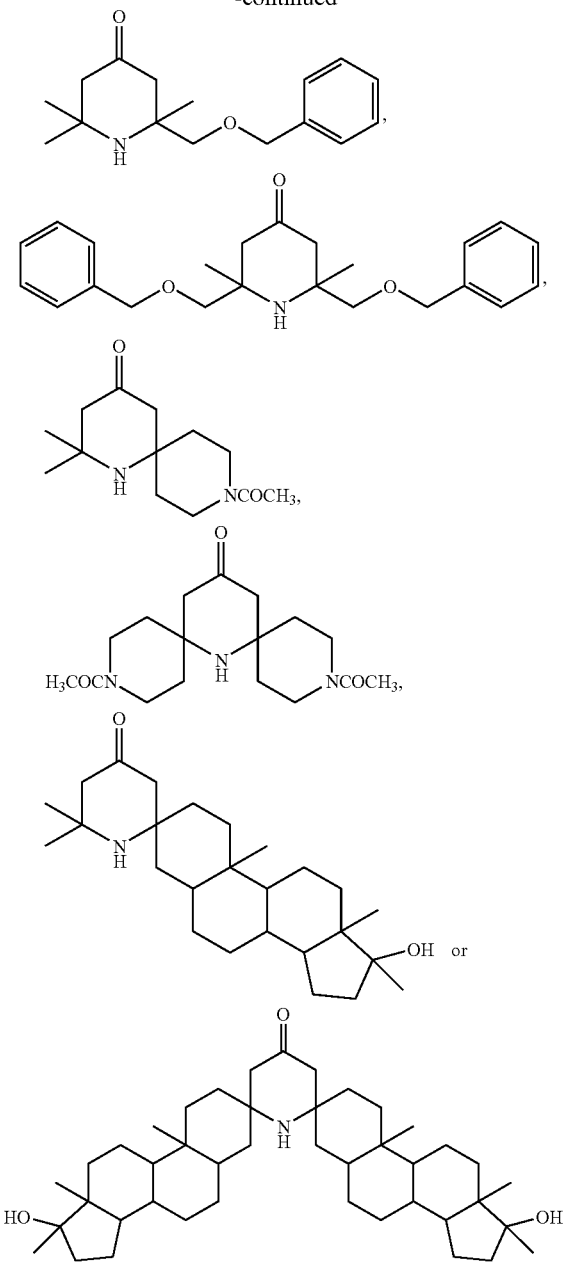

[8] The 2,6-substituted-4-piperidone derivative according to any one of items [4] to [7], wherein a nitrogen nucleus is labeled with $^{15}N$.

[9] A method for producing a nitroxyl radical derivative represented by the following formula:

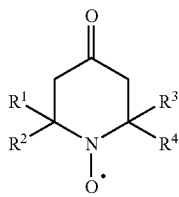

(II)

[wherein in the formula: $R^1$, $R^2$, $R^3$ and $R^4$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^1$, $R^2$, $R^3$ and $R^4$ is a group other than a hydrogen atom; and $R^1$ and $R^2$ and/or $R^3$ and $R^4$ may be independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom], wherein the method comprises the step of producing a nitroxyl radical by oxidizing an amino group of a 2,6-substituted-4-piperidone derivative obtained using the method according to any one of items [1] to [3], which is represented by the following formula:

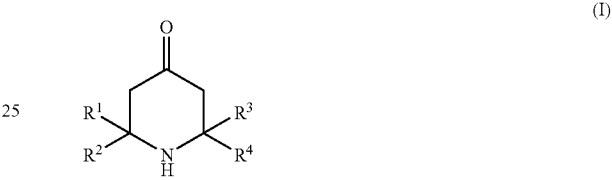

(I)

[wherein in the formula: $R^1$, $R^2$, $R^3$ and $R^4$ mean the same as described above].

[10] The production method according to item [9], wherein the nitroxyl radical derivative represented by the formula (II), the ammonium salt and the 2,6-substituted-4-piperidone derivative represented by the formula (1) are $^{15}N$-labeled compounds.

[11] A nitroxyl radical derivative, which is obtained using the method according to item [9] or [10].

[12] A nitroxyl radical derivative represented by the following formula:

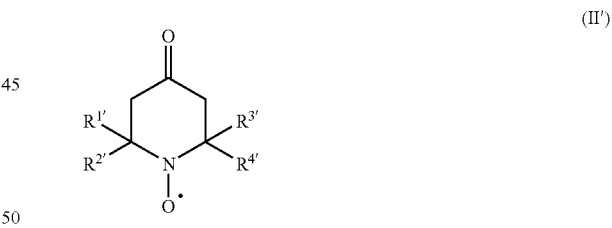

(II')

[wherein in the formula: $R^{1'}$, $R^{2'}$, $R^{3'}$ and $R^{4'}$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^{1'}$, $R^{2'}$, $R^{3'}$ and $R^{4'}$ is a group other than a hydrogen atom; and $R^{1'}$ and $R^{2'}$ and/or $R^{3'}$ and $R^{4'}$ are independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom (wherein the case where $R^{1'}$ and $R^{2'}$ and/or $R^{3'}$ and $R^{4'}$ form a cyclohexane ring with no substituent is excluded)].

[13] The nitroxyl radical derivative according to item [12], which is represented by the following formula:

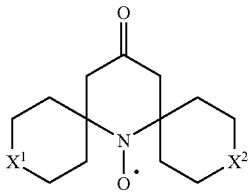
(4)

[wherein in the formula: $X^1$ and $X^2$ are each independently a substituted or unsubstituted $C_4$-$C_{20}$ cycloalkylene group which may be interrupted by an oxygen atom, a nitrogen atom or a sulfur atom; carbonyl group; acetamide group; sulfonyl group; sulfinyl group; an oxygen atom; or a sulfur atom].

[14] A nitroxyl radical derivative represented by the following formula:

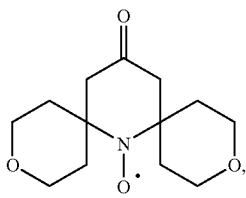

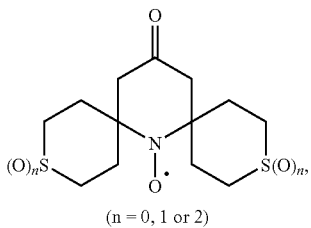
(n = 0, 1 or 2)

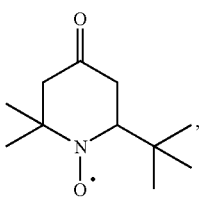

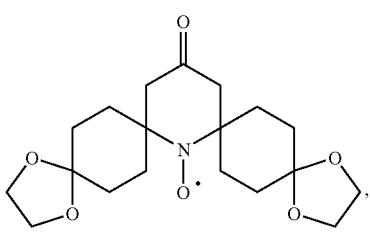

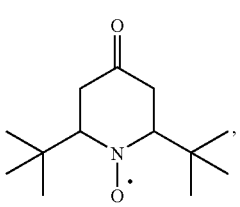

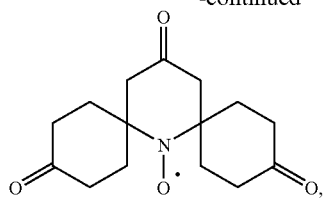

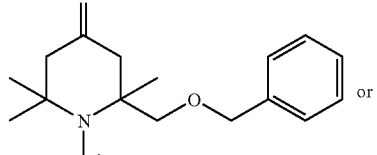
or

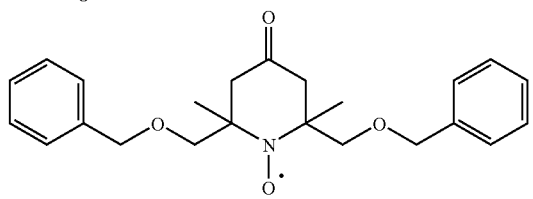

[15] The nitroxyl radical derivative according to any one of items [11] to [14], wherein a nitrogen nucleus is labeled with $^{15}N$.

According to the present invention, a 2,6-substituted-4-piperidone derivative can be obtained using a simple method. Further, according to a preferred embodiment of the present invention, by oxidizing an amino group of the obtained 2,6-substituted-4-piperidone derivative, a nitroxyl radical derivative, in which a TEMPO-based compound has substituents at position-2 and position-6, can be obtained in a high yield. According to the method, by using ammonium salt in which a nitrogen nucleus is labeled with $^{15}N$ as a raw material, a labeled compound of interest can be easily obtained. The obtained nitroxyl radical derivative and a labeled compound thereof are particularly useful, for example, as a contrast agent for following a free radical reaction in vivo.

BEST MODE FOR CARRYING OUT THE INVENTION

Figure 1:
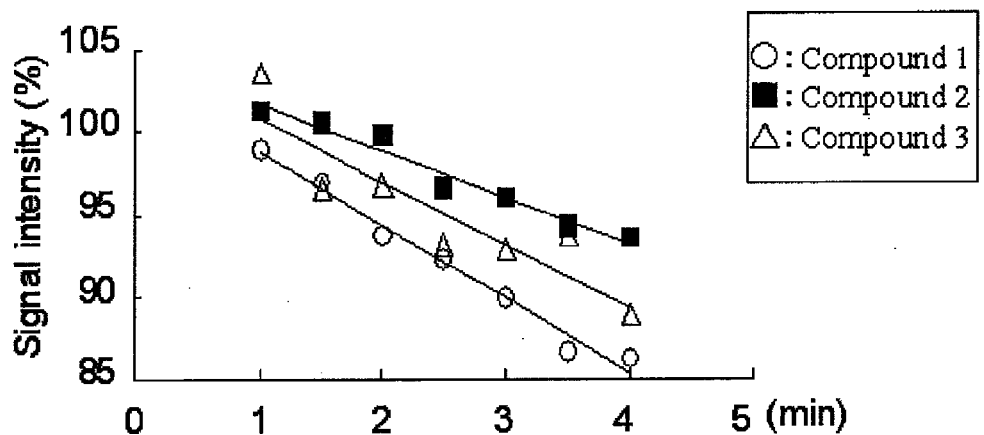
FIG. 1 is a graph for comparison between reactivities of 3 types of TEMPO-based nitroxyl radical derivatives, in which substituents at position-2 and position-6 in one derivative are different from those in another derivative, to hydroxyl radical.

Hereinafter, the present invention will be described in detail. First, the method for producing a 2,6-substituted-4-piperidone derivative of the present invention will be described.

A. Method for producing a 2,6-substituted-4-piperidone derivative

The method for producing a 2,6-substituted-4-piperidone derivative of the present invention is a method for producing a 2,6-substituted-4-piperidone derivative represented by the following formula:

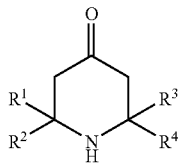
(I)

[wherein in the formula: $R^1$, $R^2$, $R^3$ and $R^4$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^1$, $R^2$, $R^3$ and $R^4$ is a group other than a hydrogen atom; and $R^1$ and $R^2$ and/or $R^3$ and $R^4$ may be independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom],
wherein the method comprises the step of reacting a triacetoneamine derivative represented by the following formula:

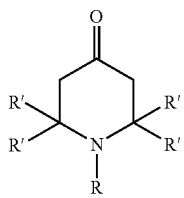
(1)

[wherein in the formula: R is a hydrogen atom or a $C_1$-$C_6$ alkyl group; and R's are each independently a $C_1$-$C_6$ alkyl group],
(in which the case where the triacetoneamine derivative represented by the formula (1) is completely identical to the 2,6-substituted-4-piperidone derivative represented by the formula (1) is excluded), with a ketone or aldehyde derivative represented by the following formula:

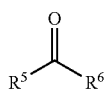
(2)

[wherein in the formula: $R^5$ and $R^6$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^5$ and $R^6$ is a group other than a hydrogen atom; and $R^5$ and $R^6$ may be crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom], in the presence of ammonium salt (hereinafter also referred to as "step A").

In the step A, as shown in the reaction scheme below, a triacetoneamine derivative (a compound represented by formula (1)) is reacted with a ketone or aldehyde derivative represented by formula (2) in the presence of ammonium salt (a compound represented by formula (i)), thereby obtaining a 2,6-substituted-4-piperidone derivative represented by formula (I):

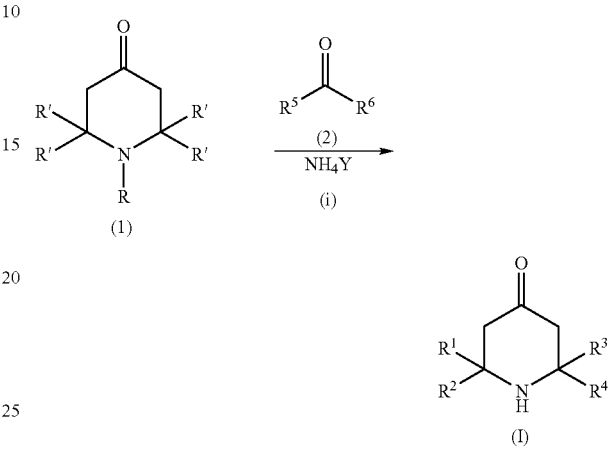

[wherein in the formulae: $R^1$, $R^2$, $R^3$, $R^4$, $R^5$, $R^6$, R and R' mean the same as described above; and Y is a halogen atom, an acetyloxy group, a trifluoroacetyloxy group, formate ($HCO_2$) or hydrogensulfate ($HSO_4$)].

The mechanism of the above-described reaction is not clear. However, when the reaction is performed using ammonium salt labeled with $^{15}N$, replacement of a nitrogen atom of a substrate occurs and a compound represented by formula (I) in which a nitrogen nucleus is labeled with $^{15}N$ is obtained in a high yield. Therefore, it is inferred that a reaction with a ketone or aldehyde derivative proceeds accompanied by transfer of an ammonia compound, as shown below.

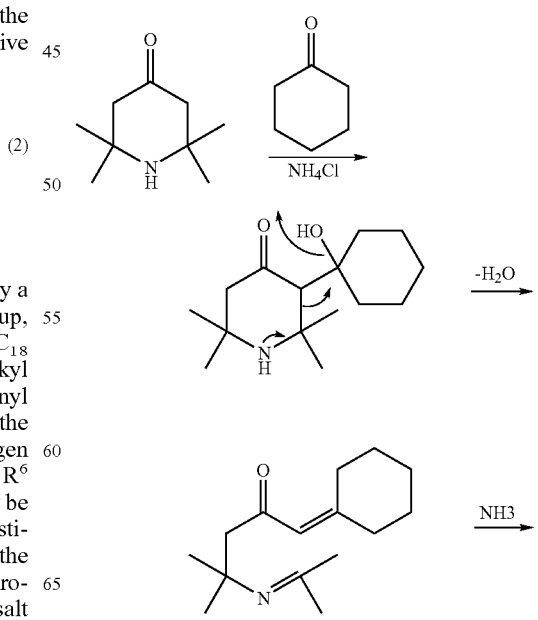

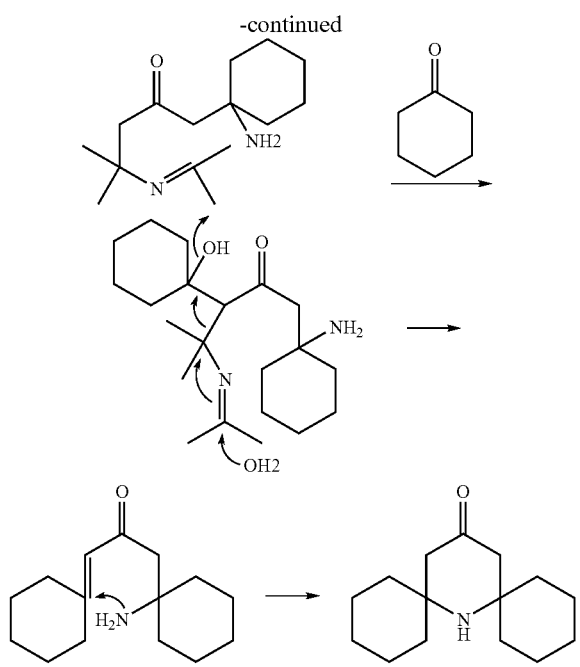

As described above, according to the present invention, by using the simple method in which a triacetoneamine derivative is reacted with a ketone or aldehyde derivative represented by formula (2) in the presence of ammonium salt, a substituent can be introduced into both or at least one of position-2 and position-6, and in addition, according to need, a nitrogen nucleus of a substrate can be labeled with $^{15}N$. The 2,6-substituted-4-piperidone derivative thus obtained is useful as an intermediate compound of a nitroxyl radical derivative or a labeled compound thereof, since such a nitroxyl radical derivative or a labeled compound thereof of interest can be easily obtained by oxidizing the 2,6-substituted-4-piperidone derivative according to the ordinary method.

(Compounds as Raw Materials)

Hereinafter, compounds as raw materials to be used in the step A will be described.

The triacetoneamine derivative to be used in the present invention is a compound represented by the following formula:

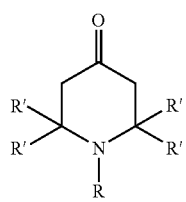

[wherein in the formula: R is a hydrogen atom or a $C_1$-$C_6$ alkyl group; and R's are each independently a $C_1$-$C_6$ alkyl group] (in which the case where the compound is completely identical to the 2,6-substituted-4-piperidone derivative represented by the aforementioned formula (I)is excluded). The "case where . . . completely identical" means the case where not only the type of substituent and the binding position, but also the steric structure, the presence or absence of isotope, etc. of the two compounds are the same.

In this regard, examples of $C_1$-$C_6$ alkyl groups include methyl group, ethyl group, propyl group, isopropyl group, n-butyl group, s-butyl group, t-butyl group, pentyl group and hexyl group. Among them, R is preferably a hydrogen atom, a methyl group or an ethyl group, and particularly preferably a methyl group. R'is preferably a methyl group or an ethyl group, and particularly preferably a methyl group.

Among triacetoneamine derivatives represented by the above-described formula (1), triacetoneamine (a compound in which R is a hydrogen atom and all R's are methyl groups) or N-methyl-triacetoneamine (a compound in which R is a methyl group and all R's are methyl groups) is preferably used on the point that these compounds are commercially available and can be easily obtained. In particular, since the 2,6-substituted-4-piperidone derivative represented by formula (1) can be obtained in a higher yield, R is preferably a methyl group, and N-methyl-triacetoneamine is preferably used. These compounds are offered commercially, for example, by Aldrich.

Regarding the ketone or aldehyde derivative represented by the above-described formula (2), in the formula: $R^5$ and $R^6$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^5$ and $R^6$ is a group other than a hydrogen atom; and $R^5$ and $R^6$ may be crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom. In particular, it is preferred that $R^5$ and $R^6$ are crosslinked to form a 5 to 8-membered ring.

In the present invention, the ketone or aldehyde derivatives represented by formula (2) may be used solely or in combination.

In this specification, the $C_1$-$C_{20}$ alkyl group is preferably a $C_1$-$C_{10}$ alkyl group. Examples of alkyl groups include methyl group, ethyl group, propyl group, isopropyl group, n-butyl group, s-butyl group, t-butyl group, pentyl group, hexyl group, octyl group, nonyl group, decyl group, undecyl group and dodecyl group.

The $C_2$-$C_{20}$ alkenyl group is preferably a $C_2$-$C_{10}$ alkenyl group. Examples of alkenyl groups include vinyl group, allyl group, propenyl group, isopropenyl group, 2-methyl-1-propenyl group, 2-methylallyl group and 2-butenyl group.

The $C_2$-$C_{20}$ alkynyl group is preferably a $C_2$-$C_{10}$ alkynyl group. Examples of alkynyl groups include ethynyl group, propynyl group and butynyl group.

The $C_4$-$C_{20}$ alkyldienyl group is preferably a $C_4$-$C_{10}$ alkyldienyl group. Examples of alkyldienyl groups include 1,3-butadienyl group.

The $C_6$-$C_{18}$ aryl group is preferably a $C_6$-$C_{10}$ aryl group. Examples of aryl groups include phenyl group, 1-naphthyl group, 2-naphthyl group, indenyl group, biphenyl group, anthryl group and phenanthryl group.

The $C_6$-$C_{20}$ alkylaryl group is preferably a $C_6$-$C_{10}$ alkylaryl group. Examples of alkylaryl groups include o-tolyl group, m-tolyl group, p-tolyl group, 2,3-xylyl group, 2,5-xylyl group, o-cumenyl group, m-cumenyl group, p-cumenyl group and mesityl group.

The $C_6$-$C_{20}$ arylalkyl group is preferably a $C_6$-$C_{10}$ arylalkyl group. Examples of arylalkyl groups include benzyl group, phenethyl group, 1-naphthylmethyl group, 2-naphthylmethyl group, 1-phenylethyl group, phenylpropyl group, phenylbutyl group, phenylpentyl group, phenylhexyl group, methylbenzyl group, dimethylbenzyl group, trimethylbenzyl group, ethylbenzyl group, methylphenethyl group, dimethylphenethyl group and diethylbenzyl group.

$C_4$-$C_{20}$ cycloalkyl group is preferably a $C_4$-$C_{10}$ cycloalkyl group. Examples of cycloalkyl groups include cyclopropyl group, cyclobutyl group, cyclopentyl group, cyclohexyl group, cycloheptyl group, and cyclooctyl group.

$C_4$-$C_{20}$ cycloalkenyl group is preferably a $C_4$-$C_{10}$ cycloalkenyl group. Examples of cycloalkenyl groups include cyclopropenyl group, cyclobutenyl group, cyclopentenyl group, cyclopentadienyl group and cyclohexenyl group.

The ($C_3$-$C_{10}$ cycloalkyl) $C_1$-$C_{10}$ alkyl group is a $C_1$-$C_{10}$ alkyl group having a $C_3$-$C_{10}$ cycloalkyl group. Examples thereof include groups consisting of a combination of a cycloalkyl group and an alkyl group selected from the aforementioned cycloalkyl groups and alkyl groups.

Note that the above-described groups may be interrupted by an oxygen atom, a nitrogen atom or a sulfur atom. When the above-described groups are interrupted by a nitrogen atom, they are preferably a group represented by —N(Z)— (wherein in the formula, Z is a hydrogen atom or a $C_1$-$C_{20}$ hydrocarbon group). In this regard, preferred examples of hydrocarbon groups include alkyl group, alkenyl group and alkynyl group. When the above-described groups are interrupted by a sulfur atom, they are preferably a group represented by —S(O)n- (wherein in the formula, n is 0, 1 or 2).

As the ketone or aldehyde derivative represented by formula (2), for example, compounds as shown below can be used, and they are commercially available and can be easily obtained.

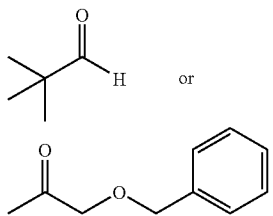

Further, $R^5$ and $R^6$ may be crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom. The aforementioned monocyclic or polycyclic saturated ring is preferably a $C_4$-$C_{20}$ monocyclic or polycyclic saturated ring. In particular, it is preferred that $R^5$ and $R^6$ are crosslinked to each other to form a 5 to 8-membered ring.

Regarding the 2,6-substituted-4-piperidone derivative obtained in the step A, $R^1$ and $R^2$ and/or $R^3$ and $R^4$ in formula (1) may be independently crosslinked to each other to form a substituted or unsubstituted $C_4$-$C_{40}$ monocyclic or polycyclic saturated ring, as in the case of $R^5$ and $R^6$, and the saturated ring may be interrupted by an oxygen atom, a nitrogen atom or a sulfur atom. The aforementioned monocyclic or polycyclic saturated ring is preferably a $C_4$-$C_{20}$ monocyclic or polycyclic saturated ring, and it is more preferred that they are crosslinked to form a 5 to 8-membered ring.

In this regard, examples of substituents include $C_1$-$C_{10}$ alkyl group, $C_2$-$C_{10}$ alkenyl group, $C_2$-$C_{10}$ alkynyl group, $C_4$-$C_{10}$ alkyldienyl group, $C_6$-$C_{10}$ aryl group, $C_6$-$C_{10}$ alkylaryl group, $C_6$-$C_{10}$ arylalkyl group, $C_4$-$C_{10}$ cycloalkyl group, $C_4$-$C_{10}$ cycloalkenyl group, ($C_3$-$C_{10}$ cycloalkyl) $C_1$-$C_{10}$ alkyl group, carbonyl group, amino group and halogen atom.

Examples of such ketone derivatives include a compound represented by the following formula:

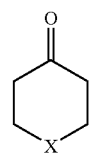

(ii)

[wherein in the formula, X is a substituted or unsubstituted alkylene group, carbonyl group, acetamide group, sulfonyl group or sulfinyl group, or an oxygen atom, or a sulfur atom].

Examples of substituents of the alkylene group include $C_1$-$C_{10}$ alkyl group, $C_2$-$C_{10}$ alkenyl group, $C_2$-$C_{10}$ alkynyl group, $C_4$-$C_{10}$ alkyldienyl group, $C_6$-$C_{10}$ aryl group, $C_6$-$C_{10}$ alkylaryl group, $C_6$-$C_{10}$ arylalkyl group, $C_4$-$C_{10}$ cycloalkyl group, $C_4$-$C_{10}$ cycloalkenyl group and ($C_3$-$C_{10}$ cycloalkyl) $C_1$-$C_{10}$ alkyl group. The alkylene group is preferably a $C_1$-$C_{20}$ alkylene group, and more preferably a $C_1$-$C_{10}$ alkylene group. Specifically, methylene group, ethylene group, trimethylene group, propylene group, etc. are preferred. Among them, methylene group is particularly preferred.

When X is a substituted or unsubstituted alkylene group, X will have two substituents. These substituents may be crosslinked to each other to form a substituted or unsubstituted $C_4$-$C_{20}$ monocyclic or polycyclic saturated ring, and the saturated ring may be interrupted by an oxygen atom, a nitrogen atom or a sulfur atom. As the substituents, the same substituents as those for $R^5$ and $R^6$ can be used. When the aforementioned saturated ring is interrupted by a nitrogen atom, it is preferably a group represented by —N(Z)— (wherein in the formula, Z is a hydrogen atom or a $C_1$-$C_{20}$ hydrocarbon group). In this regard, preferred examples of hydrocarbon groups include alkyl group, alkenyl group and alkynyl group. When these groups are interrupted by a sulfur atom, they are preferably a group represented by —S(O)n- (wherein in the formula, n is 0, 1 or 2).

As the compound represented by formula (ii), for example, compounds as shown below can be used, and they are commercially available and can be easily obtained.

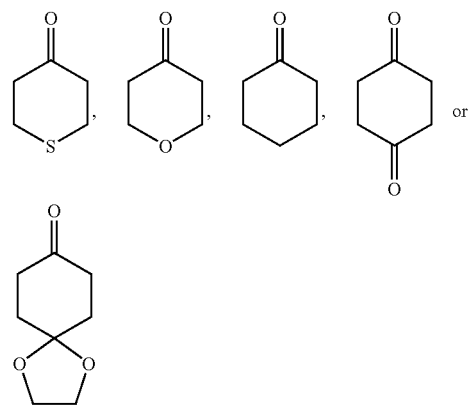

The use amount of the ketone or aldehyde derivative represented by formula (2) is preferably 1.0 to 10.0 equivalents, more preferably 2.0 to 5.0 equivalents, and particularly preferably 2.0 to 3.0 equivalents per 1 equivalent of triacetoneamine derivative.

Ammonium salt to be used in the present invention is not particularly limited, but those which can develop a reaction under relatively mild conditions are preferably used. For example, compounds represented by the following formula:

NH$_4$Y    (i)

[wherein in the formula, Y is a halogen atom, an acetyloxy group, a trifluoroacetyloxy group, formate (HCO$_2$) or hydrogensulfate (HSO$_4$)] can be used. In this regard, examples of halogen atoms include fluorine, chlorine, bromine and iodine, and chlorine or bromine is particularly preferred. More specifically, ammonium chloride salt, ammonium bromide salt, ammonium acetate salt, ammonium trifluoroacetate salt, ammonium formate salt, ammonium hydrogen sulfate salt, etc. are preferably used.

When obtaining a labeled compound, ammonium salt in which a nitrogen nucleus is labeled with $^{15}$N is used. By using a $^{15}$N-labeled compound of ammonium salt, the 2,6-substituted-4-piperidone derivative can be easily labeled.

The use amount of ammonium salt is preferably 2.0 to 10.0 equivalents, more preferably 3.0 to 8.0 equivalents, and particularly preferably 5.0 to 7.0 equivalents per 1 equivalent of triacetoneamine derivative.

In the step A, compounds as raw materials such as the triacetoneamine derivative, the ketone or aldehyde derivative represented by formula (2) and ammonium salt are mixed in a solvent to cause a reaction. A reaction solvent is not particularly limited as long as it is inactive with respect to these compounds. For example, organic solvents such as DMSO, DMF, THF, dioxane, methanol, ethanol and propanol are preferably used.

(Reaction Conditions)

Next, reaction conditions will be described.

The reaction in the step A can be performed under relatively mild conditions. The reaction temperature is preferably room temperature to 90° C., more preferably 50 to 80° C., and particularly preferably 60 to 70° C.

The reaction time may be suitably determined based on confirmation of extent of reaction, but is usually about 3 to 20 hours, preferably 5 to 15 hours, and more preferably 6 to 10 hours.

Further, the step A can be carried out under increased pressure, reduced pressure or atmospheric pressure. However, in view of easiness of operation, it is desired that the step A is carried out under atmospheric pressure.

After completion of the reaction, a product is separated/extracted from the reaction solution and purified according to the ordinary method, thereby obtaining a 2,6-substituted-4-piperidone derivative of interest.

In the step A, using the simple method as described above, substituents can be introduced into position-2 and position-6 of 4-piperidone. Therefore, it is possible to easily obtain 2,6-substituted-4-piperidone derivatives with various properties. Further, by using ammonium salt in which a nitrogen nucleus is labeled with $^{15}$N, a $^{15}$N-labeled compound of 2,6-substituted-4-piperidone derivative can be obtained in a high yield. Therefore, the present invention has the advantage that the production process can be more simplified compared to the conventional method. Moreover, the $^{15}$N-labeled compound of 2,6-substituted-4-piperidone derivative can also be easily produced in a high yield by changing one of the compounds as raw materials to be used in the step A to a $^{15}$N-labeled compound thereof. The present invention also includes compounds obtained in such a manner.

In particular, in the present invention, 2,6-substituted-4-piperidone derivatives represented by the following formula:

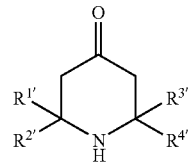

(I')

[wherein in the formula: R$^{1'}$, R$^{2'}$, R$^{3'}$ and R$^{4'}$ are each independently a hydrogen atom, a C$_1$-C$_{20}$ alkyl group, a C$_2$-C$_{20}$ alkenyl group, a C$_2$-C$_{20}$ alkynyl group, a C$_4$-C$_{20}$ alkyldienyl group, a C$_6$-C$_{18}$ aryl group, a C$_6$-C$_{20}$ alkylaryl group, a C$_6$-C$_{20}$ arylalkyl group, a C$_4$-C$_{20}$ cycloalkyl group, a C$_4$-C$_{20}$ cycloalkenyl group, or a (C$_3$-C$_{10}$ cycloalkyl) C$_1$-C$_{10}$ alkyl group, and the aforementioned groups may be interrupted by an oxygen atom, a nitrogen atom or a sulfur atom; any one of R$^{1'}$, R$^{2'}$, R$^{3'}$ and R$^{4'}$ is a group other than a hydrogen atom; and R$^{1'}$ and R$^{2'}$ and/or R$^{3'}$ and R$^{4'}$ are independently crosslinked to each other to form a substituted or unsubstituted C$_4$-C$_{40}$ monocyclic or polycyclic saturated ring, and the saturated ring may be interrupted by an oxygen atom, a nitrogen atom or a sulfur atom (wherein the case where R$^{1'}$ and R$^{2'}$ and/or R$^{3'}$ and R$^{4'}$ form a cyclohexane ring with no substituent is excluded)] are preferred. There is a possibility that these compounds exhibit properties different from those of conventional compounds, and therefore, application to various uses is expected.

Among such compounds, compounds represented by the following formula:

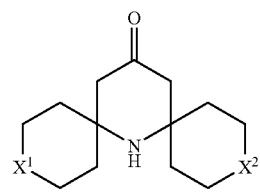

(3)

[wherein in the formula, X$^1$ and X$^2$ are each independently a substituted or unsubstituted C$_4$-C$_{20}$ cycloalkylene group which may be interrupted by an oxygen atom, a nitrogen atom or a sulfur atom; carbonyl group; acetamide group; sulfonyl group; sulfinyl group; an oxygen atom; or a sulfur atom] are preferred. Note that X$^1$ and X$^2$ are the limitation of the aforementioned X, and examples of substituents for X$^1$ and X$^2$ and preferred examples of X$^1$ and X$^2$ are the same as those of the aforementioned X. Therefore, explanation thereof is omitted herein.

More specifically, preferred examples of 2,6-substituted-4-piperidone derivatives obtained using the method of the present invention include the following compounds:

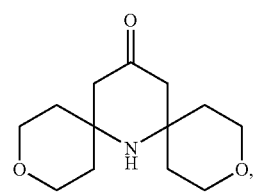

-continued

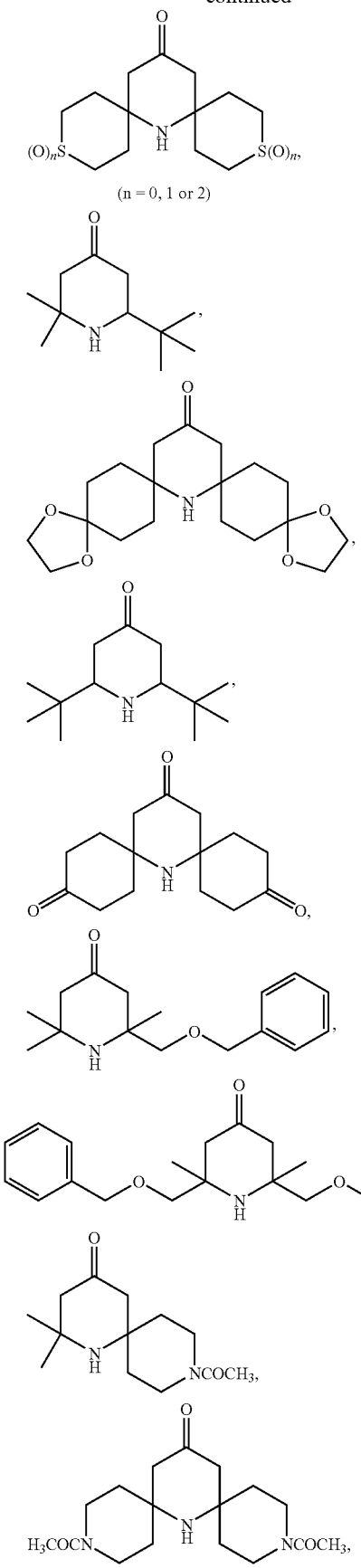

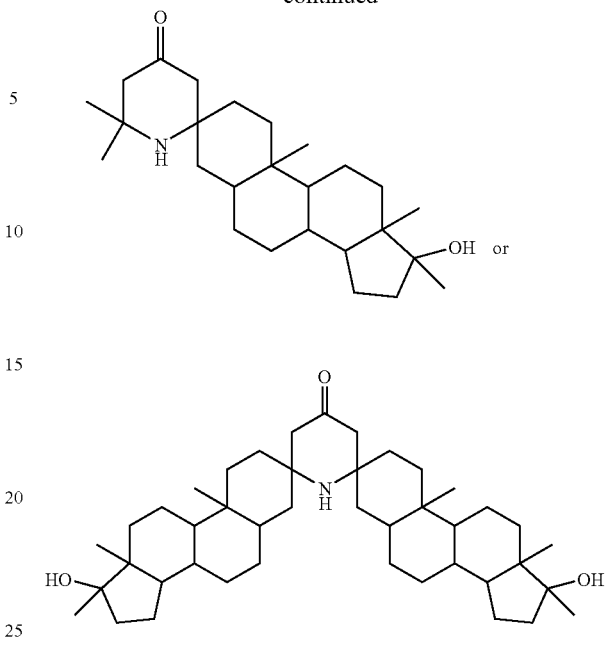

Among the above-described 2,6-substituted-4-piperidone derivatives, $^{15}$N-labeled compounds thereof in which a nitrogen nucleus is labeled with $^{15}$N are preferred.

B. Method for Producing Nitroxyl Radical Derivative

Next, the method for producing a nitroxyl radical derivative of the present invention will be described.

The present invention provides a method for producing a nitroxyl radical derivative represented by the following formula:

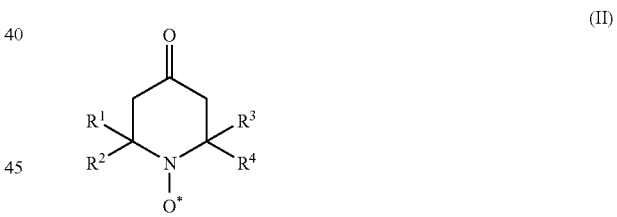

(II)

[wherein in the formula: $R^1$, $R^2$, $R^3$ and $R^4$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^1$, $R^2$, $R^3$ and $R^4$ is a group other than a hydrogen atom; and $R^1$ and $R^2$ and/or $R^3$ and $R^4$ may be independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom], wherein the method comprises the step of oxidizing an amino group of the 2,6-substituted-4-piperidone derivative obtained in the aforementioned step A, which is represented by the following formula:

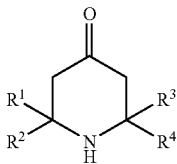

(I)

[wherein in the formula, $R^1$, $R^2$, $R^3$ and $R^4$ mean the same as described above], to produce a nitroxyl radical (hereinafter also referred to as "step B").

In the step B, as shown in the reaction scheme below, an amino group of the 2,6-substituted-4-piperidone derivative obtained in the aforementioned step A of the "method for producing a 2,6-substituted-4-piperidone derivative" is oxidized, thereby obtaining a nitroxyl radical:

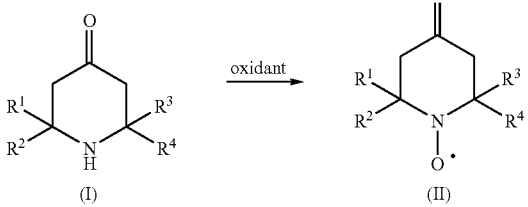

[wherein in the formula, $R^1$, $R^2$, $R^3$ and $R^4$ mean the same as described above].

According to the step B, substituents can be introduced into position-2 and position-6 of a TEMPO-based compound using a simple method. Further, when using a labeled compound of the 2,6-substituted-4-piperidone derivative, a labeled compound of a nitroxyl radical derivative of interest can be obtained in a high yield.

(Compounds as Raw Materials)

Examples of oxidants to be used in the step B include hydrogen peroxide, perbenzoic acids such as m-chloroperbenzoic acid, peracetic acid, periodic acid and oxonic acid. Among them, hydrogen peroxide is preferably used, and 30% hydrogen peroxide is particularly preferably used. The use amount of the oxidant is preferably 3 to 50 equivalents, more preferably 5 to 15 equivalents, and particularly preferably 7 to 10 equivalents per 1 equivalent of 2,6-substituted-4-piperidone.

In the step B, an oxidation catalyst can be employed for a combination use. Examples of oxidation catalysts that can be used in the step B include sodium tungstate and methyltrioctylammonium hydrogen sulfate.

The reaction is preferably performed in a solvent. The solvent is not particularly limited as long as it is inactive with respect to the 2,6-substituted-4-piperidone derivative. Preferred examples thereof include organic solvent such as alcohols (for example, alcohol and methanol), chloroform and dichloromethane.

(Reaction Conditions)

Next, reaction conditions in the step B will be described.

In the step B, the reaction temperature is preferably 0 to 30° C., more preferably 15 to 30° C., and particularly preferably 20 to 25° C.

The reaction time may be suitably determined based on confirmation of extent of reaction, but is usually about 10 to 40 hours, preferably 15 to 30 hours, and more preferably 20 to 25 hours.

Further, the step B can be carried out under increased pressure, reduced pressure or atmospheric pressure. However, in view of easiness of operation, it is desired that the step B is carried out under atmospheric pressure.

After completion of the reaction, a product is separated/extracted from the reaction solution and purified according to the ordinary method, thereby obtaining a nitroxyl radical derivative of interest.

According to the method of the present invention, by using the simple method in which an amino group of the 2,6-substituted-4-piperidone derivative is oxidized, the nitroxyl radical derivative represented by the following formula:

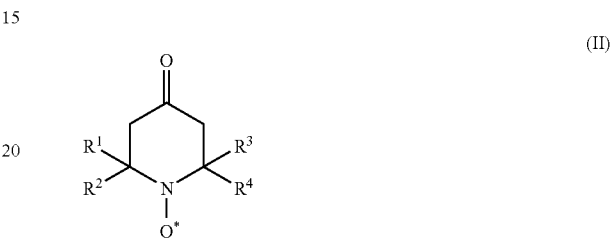

(II)

[wherein in the formula: $R^1$, $R^2$, $R^3$ and $R^4$ mean the same as described above] can be obtained in a high yield. Moreover, by using a $^{15}$N-labeled compound of the 2,6-substituted-4-piperidone derivative, a $^{15}$N-labeled compound of the nitroxyl radical derivative can also be easily obtained in a high yield. The present invention also includes compounds obtained in such a manner.

In particular, in the present invention, nitroxyl radical derivatives represented by the following formula:

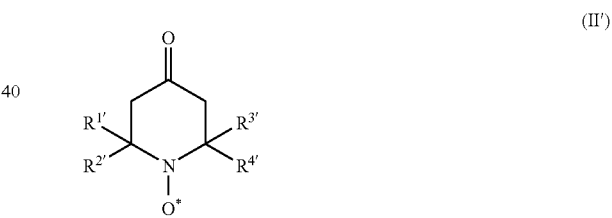

(II')

[wherein in the formula: $R^{1'}$, $R^{2'}$, $R^{3'}$ and $R^{4'}$ are each independently a hydrogen atom, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, or a ($C_3$-$C_{10}$ cycloalkyl) $C_1$-$C_{10}$ alkyl group, and the aforementioned groups may be interrupted by an oxygen atom, a nitrogen atom or a sulfur atom; any one of $R^{1'}$, $R^{2'}$, $R^{3'}$ and $R^{4'}$ is a group other than a hydrogen atom; and $R^{1'}$ and $R^{2'}$ and/or $R^{3'}$ and $R^{4'}$ are independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom (wherein the case where $R^{1'}$ and $R^{2'}$ and/or $R^{3'}$ and $R^{4'}$ independently than a cyclohexane ring with no substituent is excluded)] are preferred. There is a possibility that these compounds exhibit properties different from those of conventional compounds, and therefore, application to various uses is expected.

Among such compounds, nitroxyl radical derivatives represented by the following formula:

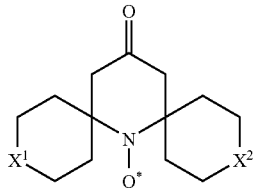

(4)

[wherein in the formula, $X^1$ and $X^2$ are each independently a substituted or unsubstituted $C_4$-$C_{20}$ cycloalkylene group which may be interrupted by an oxygen atom, a nitrogen atom or a sulfur atom; carbonyl group; acetamide group; sulfonyl group; sulfinyl group; an oxygen atom; or a sulfur atom] are preferred. Note that $X^1$ and $X^2$ are the limitation of the aforementioned X, and examples of substituents for $X^1$ and $X^2$ and preferred examples of $X^1$ and $X^2$ are the same as those of the aforementioned X. Therefore, explanation thereof is omitted herein.

More specifically, preferred examples of nitroxyl radical derivatives obtained using the method of the present invention include the following compounds:

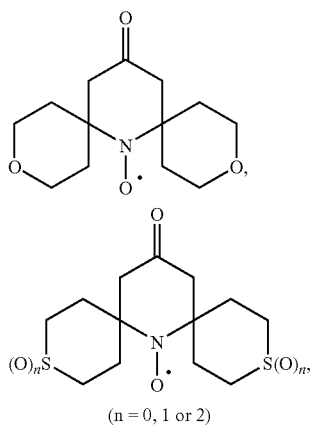

(n = 0, 1 or 2)

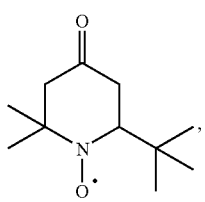

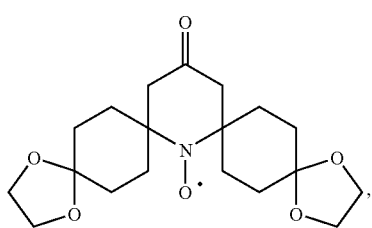

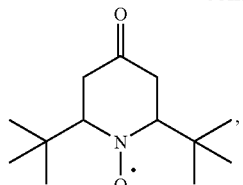

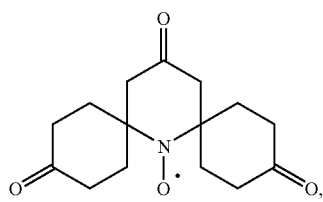

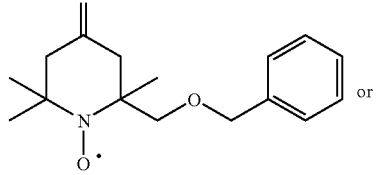

or

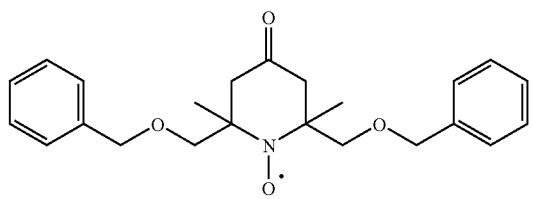

Among the above-described nitroxyl radical derivatives, $^{15}$N-labeled compounds thereof in which a nitrogen nucleus is labeled with $^{15}$N are preferred.

The nitroxyl radical derivative of the present invention can be widely used as an antioxidative agent, a chemical cell, a polymerization agent or the like. In particular, the nitroxyl radical derivative of the present invention is useful as a contrast agent for following a free radical reaction in vivo, utilizing its high sensitivity to a free radical such as active oxygen. Regarding a nitroxyl radical derivative administered to a living body, the distribution, etc. therein vary depending on the basic structure and the type of substituent. When attention is focused on this point, it is possible to perform image analysis in vivo by labeling a nitrogen nucleus of each of nitroxyl radical derivatives having different distribution properties in vivo with $^{14}$N or $^{15}$N to distinguish the information obtained by $^{14}$N from the information obtained by $^{15}$N for analysis. The present inventors already developed the simultaneous separating imaging method using a $^{14}$N-labeled or $^{15}$N-labeled compound of the nitroxyl radical derivative (see Non-patent document 1: H. Utsumi, K. Yamada, K. Ichikawa, K. Sakai, Y. Kinoshita, S. Matsumoto and M. Nagai, PNAS, 103, 1463 (2006)). According to the present invention, nitroxyl radical derivatives with various distribution properties in vivo, which are useful for the image analysis in vivo, can be produced using the simple method.

EXAMPLES

Hereinafter, the present invention will be more specifically described by way of examples. However, the present invention is not limited only to these examples.

Example 1

Synthesis of 2,6-spirocyclohexyl piperidine-4-one 1-oxyl (Step A)

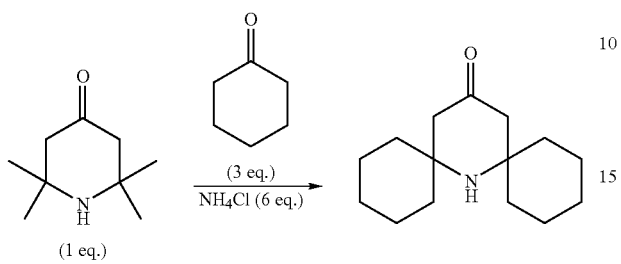

1.55 g (1 eq.) of triacetoneamine, 3.21 g (6 eq.) of NH$_4$Cl and 2.94 g (3 eq.) of cyclohexanone were mixed in a DMSO solvent (20 ml), and the mixture was heated and stirred at 60° C. for 15 to 20 hours. After a reaction, the solution was diluted with water (40 ml), and was made acidic with 7% hydrochloric acid (10 ml). The neutral portion was extracted and removed using ether. The pH of the mother liquid was adjusted to 9 to 10 using 10% aqueous solution of potassium carbonate, and extraction with ethyl acetate was carried out 3 times. The extracted ethyl acetate layers were gathered, washed with saline twice, and thereafter dried with anhydrous sodium sulfate. The solvent was removed under reduced pressure. The obtained oily substance was purified using silica gel column chromatography (developing solvent; ethyl acetate: hexane). The obtained crystal was recrystallized from hexane-ethyl acetate, thereby obtaining 380 mg of 2,6-spirocyclohexyl piperidine-4-one (yield: 16%).

Melting point: 103° C.

$^1$HNMR (CDCl$_3$) δ 1.35~1.60 (20H), 2.30 (4H, s, —CH$_2$COCH$_2$—).

FAB-MS m/z 236.3 ($^+$M+1)

(Step B)

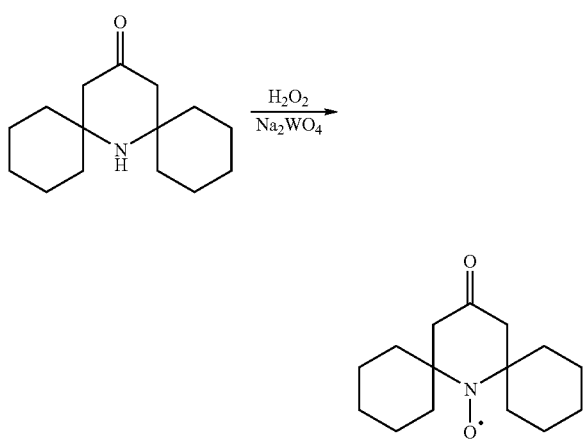

235 mg of 2,6-spirocyclohexyl piperidine-4-one obtained in the aforementioned step was dissolved in methanol (10 ml), and to this mixture, 30% H$_2$O$_2$ (2 ml), and subsequently Na$_2$WO$_4$ (50 mg) dissolved in water (1 ml) were added, and the mixture was stirred at room temperature for 20 hours. After a reaction, 10% acidic aqueous solution of sodium sulfite (20 ml) was added to the mixture, followed by stirring for 10 minutes. After that, water (20 ml) was added thereto, and extraction with chloroform was carried out 3 times. After dried with salt cake, the solvent was distilled away under reduced pressure, and the obtained crystal was recrystallized from hexane, thereby obtaining 208 mg of 2,6-spirocyclohexyl piperidine-4-one 1-oxyl (yield: 83%).

Melting point: 116.5° C.

FAB-MS m/z 251.3 ($^+$M+1)

Example 2

Synthesis of 2,6-spirocyclohexyl piperidine-4-one 1-oxyl (Step A)

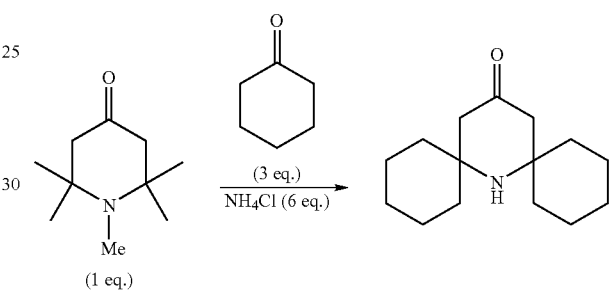

1.69 g (1 eq.) of N-methyl-triacetoneamine, 3.21 g (6 eq.) of NH$_4$Cl and 2.94 g (3 eq.) of cyclohexanone were mixed in a DMSO solvent (20 ml), and the mixture was stirred at 60° C. for 5 hours. The reaction solution was diluted with water (40 ml), and was made acidic with 7% hydrochloric acid (10 ml). The neutral portion was extracted and removed using ether. The pH of the mother liquid was adjusted to 9 to 10 using 10% aqueous solution of potassium carbonate, and extraction with ethyl acetate was carried out 3 times. The extracted ethyl acetate phases were gathered, washed with saline twice, and thereafter dried with anhydrous sodium sulfate. The solvent was removed under reduced pressure. The obtained oily substance was purified using silica gel column chromatography (developing solvent; hexane:acetate ester). The obtained crystal was recrystallized from ethyl acetate-hexane, thereby obtaining 788 mg of 2,6-spirocyclohexyl piperidine-4-one (yield: 34%).

(Step B)

295 mg of 2,6-spirocyclohexyl piperidine-4-one 1-oxyl was obtained in a manner similar to that in Step B of Example 1 (yield: 82%).

By comparing the result in Example 1 with that in Example 2, it was found that, when using N-methyl-triacetoneamine in place of triacetoneamine as a starting material, the yield of 2,6-spirocyclohexyl piperidine-4-one in Step A increased about twice.

Example 3

Synthesis of bis(tetrahydropyran-4'-spiro)-2,6-piperidine-4-one 1-oxyl (Step A)

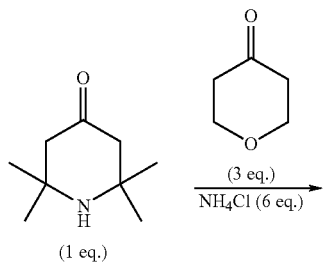

1.55 g (1 eq.) of triacetoneamine, 3.21 g (6 eq.) of NH$_4$Cl and 3.00 g (3 eq.) of 4-oxotetrahydropyran were mixed in a DMSO solvent (10 ml), and the mixture was stirred at 60° C. for 15 to 20 hours. The reaction solution was diluted with water (40 ml), and was made acidic with 7% hydrochloric acid (10 ml). The neutral portion was extracted and removed using ether. The pH of the mother liquid was adjusted to 9 to 10 using 10% aqueous solution of potassium carbonate, and extraction with chloroform was carried out 3 times. The extracted chloroform phases were gathered, washed with saline twice, and thereafter dried with salt cake to remove the solvent. The obtained oily substance was purified using silica gel column chromatography (developing solvent; hexane:acetate ester:methanol). The obtained crystal was recrystallized from hexane-acetate ester, thereby obtaining 340 mg of bis(tetrahydropyran-4'-spiro)-2,6-piperidine-4-one (yield: 14%).

Melting point: 167° C.

$^1$HNMR (CDCl$_3$) δ 1.60~1.68 (8H, brs, CH$_2$×4), 2.40 (4H, s, —CH$_2$COCH$_2$—), 3.56 (4H, m, —CH$_2$OCH$_2$—), 3.82 (4H, m, —CH$_2$OCH$_2$—).

FAB-MS m/z 240.3 ($^+$M+1)

(Step B)

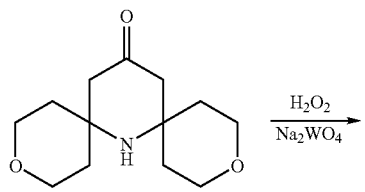

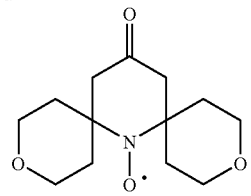

130 mg of bis(tetrahydropyran-4'-spiro)-2,6-piperidine-4-one obtained in the aforementioned step, 30% H$_2$O$_2$ (0.8 ml) and Na$_2$WO$_4$ (30 mg) were mixed in a solvent of methanol (5 ml), and the mixture was stirred at room temperature for 20 hours. 10% acidic aqueous solution of sodium sulfite (10 ml) was added to the mixture, followed by stirring for 10 minutes. After that, water (10 ml) was added thereto, and extraction with chloroform was carried out (3 times). After dried with salt cake, the solvent was distilled away under reduced pressure, and the obtained crystal was recrystallized from ethyl acetate, thereby obtaining 110 mg of bis(tetrahydropyran-4'-spiro)-2,6-piperidine-4-one 1-oxyl.

Melting point: 145.9° C.

FAB-MS m/z 255.3 ($^+$M+1)

Example 4

Synthesis of $^{15}$N-labeled compound of 2,6-spirocyclohexyl piperidine-4-one 1-oxyl A reaction was performed in a manner similar to that in Example 2, except that $^{15}$NH$_4$Cl in which the nitrogen nucleus is labeled with $^{15}$N was used instead of NH$_4$Cl. As a result, in Step A, 780 mg of $^{15}$N-labeled compound of 2,6-spirocyclohexyl piperidine-4-one was obtained (yield: 34%).

Melting point: 100.4° C.

$^1$HNMR (CDCl$_3$) δ 1.35~1.60 (20H), 2.30 (4H, s, —CH$_2$COCH$_2$—).

FAB-MS m/z 237.3 ($^+$M+1)

In Step B, 430 mg of 2,6-spirocyclohexyl piperidine-4-one 1-oxyl was obtained (yield: 80%).

Melting point: 117.4° C.

FAB-MS m/z 251.3 ($^+$M+1)

Example 5

Synthesis of $^{15}$N-labeled compound of bis(tetrahydropyran-4'-spiro)-2,6-piperidine-4-one 1-oxyl A reaction was performed in a manner similar to that in Example 3, except that 1.69 g (1 eq.) of N-methyl-triacetoneamine and $^{15}$NH$_4$Cl in which the nitrogen nucleus is labeled with $^{15}$N were used instead of triacetoneamine and NH$_4$Cl, respectively. As a result, in Step A, 760 mg of bis(tetrahydropyran-4'-spiro)-2,6-piperidine-4-one was obtained (yield: 32%).

Melting point: 167° C.

$^1$HNMR (CDCl$_3$) δ 1.60~1.68 (8H, brs, CH$_2$×4), 2.40 (4H, s, —CH$_2$COCH$_2$—), 3.56 (4H, m, —CH$_2$OCH$_2$—), 3.82 (4H, m, —CH$_2$OCH$_2$—).

FAB-MS m/z 241.2 ($^+$M+1)

In Step B, 105 mg of $^{15}$N-labeled compound of bis(tetrahydropyran-4'-spiro)-2,6-piperidine-4-one 1-oxyl was obtained (yield: 75%).

Example 6

Synthesis of bis(tetrahydrothiopyran-4'-spiro)-2,6-piperidine-4-one (Step A)

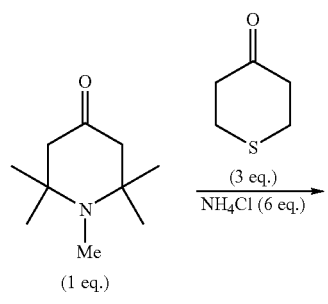

A reaction was performed in a manner similar to that in Step A of Example 2, except that 3.48 g (3 eq.) of tetrahydrothiopyran-4-one was used instead of cyclohexanone. As a result, 813 mg of bis(tetrahydrothiopyran-4'-spiro)-2,6-piperidine-4-one was obtained (yield: 30%).

Melting point: 155 to 157° C.
$^1$HNMR (CDCl$_3$) δ 1.76~1.90 (8H, m, CH$_2$×4), 2.29 (4H, s, —CH$_2$COCH$_2$—), 2.42~2.50 (4H, m, —CH$_2$SCH$_2$—), 2.88~2.96 (4H, m, —CH$_2$SCH$_2$—).
FAB-MS m/z 272.2 ($^+$M+1)

Example 7

Synthesis of bis(tetrahydrosulfinylpyran-4'-spiro)-2,6-piperidine-4-one 1-oxyl and bis(tetrahydrosulfonylpyran-4'-spiro)-2,6-piperidine-4-one 1-oxyl

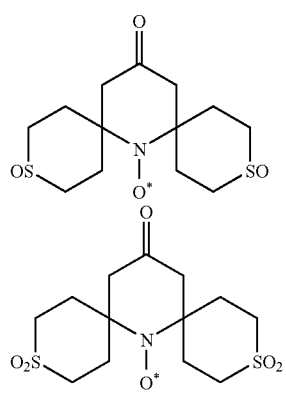

In a manner similar to that in Step B of Example 1, 250 mg of bis(tetrahydrothiopyran-4'-spiro)-2,6-piperidine-4-one, 30% H$_2$O$_2$ (2 ml) and Na$_2$WO$_4$ (50 mg) dissolved in water (1.5 ml) were mixed in methanol (8 ml), and the mixture was stirred at room temperature for 20 hours. After a reaction, 10% acidic aqueous solution of sodium sulfite (20 ml) was added to the mixture, followed by stirring for 10 minutes. After that, water (20 ml) was added thereto, and extraction with chloroform was carried out 3 times. After dried with salt cake, the solvent was distilled away under reduced pressure, thereby obtaining a mixture of water-soluble bis(tetrahydrosulfinylpyran-4'-spiro)-2,6-piperidine-4-one 1-oxyl and bis(tetrahydrosulfonylpyran-4'-spiro)-2,6-piperidine-4-one 1-oxyl.

Example 8

Synthesis of bis(1'-ethylenedioxycyclohexane-4'-spiro)-2,6-piperidine-4-one

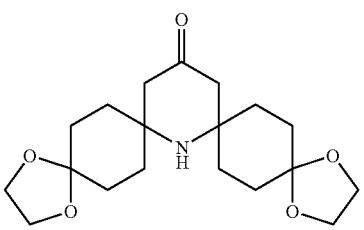 [SMILES: O=C1CC2(CCC3(CC2)OCCO3)NC2(CCC3(CC2)OCCO3)C1]

A reaction was performed in a manner similar to that in Step A of Example 2, except that 4.68 g (3 eq.) of 1,4-cyclohexanedione monoethyleneacetal was used instead of cyclohexanone. As a result, 1.12 g of bis(1'-ethylenedioxycyclohexane-4'-spiro)-2,6-piperidine-4-one was obtained (yield: 32%).

Melting point: 190.6° C.
$^1$HNMR (CDCl$_3$) δ 1.50~1.91 (16H, brt, CH$_2$×8), 2.35 (4H, s, —CH$_2$COCH$_2$—), 3.90 (8H, brs, —OCH$_2$×4).
FAB-MS m/z 352.4 ($^+$M+1)

Example 9

Synthesis of bis(1'-oxocyclohexane-4'-spiro)-2,6-piperidine-4-one

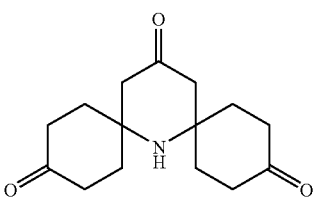 [SMILES: O=C1CCC2(CC1)CC(=O)CC1(CCC(=O)CC1)N2]

536 mg of bis(1'-ethylenedioxycyclohexane-4'-spiro)-2,6-piperidine-4-one was dissolved in acetic acid (7 ml) and water (2 ml), 5 drops of concentrated hydrochloric acid was added thereto, and the mixture was stirred at 60° C. for 5 hours. After a reaction, water (30 ml) was added thereto, and the pH thereof was adjusted to 8 using 5% potassium carbonate solution, followed by extraction with chloroform 4 times. After dried with salt cake, the solvent was distilled away under reduced pressure. The obtained oily substance was purified using silica gel column chromatography (developing solvent; acetate ester:hexane). The obtained crystal was recrystallized from ethyl acetate-hexane, thereby obtaining 330 mg of bis(1'-oxocyclohexane-4'-spiro)-2,6-piperidine-4-one (yield: 82%).

Melting point: 155.3° C.

$^1$HNMR (CDCl$_3$) δ 1.82~1.94 (4H, m, CH$_2$×2), 2.00~2.06 (4H, m, CH$_2$×2), 2.26~2.36 (4H, m, —CH$_2$COCH$_2$—), 2.48 (4H, d, —CH$_2$COCH$_2$—), 2.58~2.68 (4H, m, —CH$_2$COCH$_2$—).

FAB-MS m/z 264.2 ($^+$M+1)

Example 10

Synthesis of bis(1'-oxocyclohexane-4'-spiro)-2,6-piperidine-4-one 1-oxyl

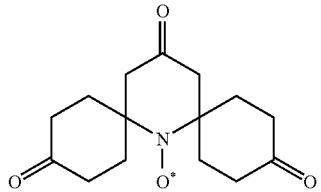

In a manner similar to that in Step B of Example 1, using 215 mg of bis(1'-oxocyclohexane-4'-spiro)-2,6-piperidine-4-one, 170 mg of bis(1'-oxocyclohexane-4'-spiro)-2,6-piperidine-4-one 1-oxyl was obtained (yield: 75%).

Melting point: 161.5° C.

FAB-MS m/z 279.2 ($^+$M+1)

Example 11

Synthesis of 2,6-dimethyl-2,6-benzyloxymethyl-4-piperidone and 2,2,6-trimethyl-benzyloxymethyl-4-piperidone

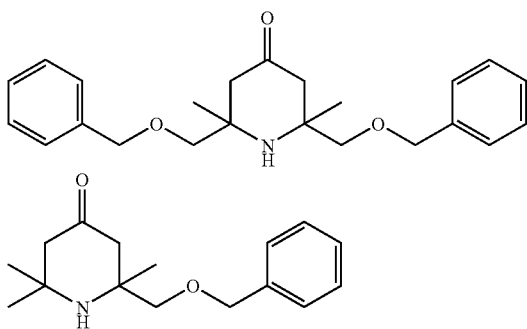

A reaction was performed in a manner similar to that in Step A of Example 2, except that 4.92 g (3 eq.) of benzyloxyacetone was used instead of cyclohexanone. As a result, 2,6-dimethyl-2,6-benzyloxymethyl-4-piperidone and 2,2,6-trimethyl-benzyloxymethyl-4-piperidone were obtained. Oily substances were separated using silica gel column chromatography (developing solvent; hexane:ethyl acetate), thereby obtaining 410 mg of oily substance of 2,6-dimethyl-2,6-benzyloxymethyl-4-piperidone (yield: 12%) and 512 mg of oily substance of 2,2,6-trimethyl-benzyloxymethyl-4-piperidone (yield: 20%).

2,6-dimethyl-2,6-benzyloxymethyl-4-piperidone $^1$HNMR (CDCl$_3$) δ 1.08~1.15 (m) 6H (CH$_3$×2), 2.10~2.50 (4H, m, —CH$_2$COCH$_2$—), 3.05~3.50 (4H, m, —OCH$_2$—×2), 4.20~4.60 (4H, m, CH$_2$O×2), 7.30 (10H, brs, aromatic-H).

FAB-MS m/z 368.3 ($^+$M+1)

2,2,6-trimethyl-benzyloxymethyl-4-piperidone $^1$HNMR (CDCl$_3$) δ 1.05~1.13 (9H, m, CH$_3$×3), 2.08~2.30 (4H, m, —CH$_2$COCH$_2$—), 2.60 (1H, m, N—CH), 3.18~3.30 (2H, m, —CH$_2$O—), 4.40~4.60 (2H, m, —CH$_2$O—), 7.30 (5H, brs, aromatic H).

FAB-MS m/z 262.3 ($^+$M+1)

Example 12

Synthesis of 2,6-di-t-butyl-4-piperidone and 2,2-dimethyl-6-t-butyl-4-piperidone

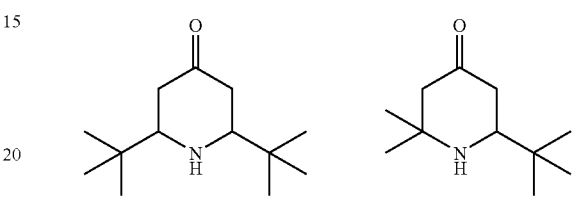

A reaction was performed in a manner similar to that in Step A of Example 2, except that 2.58 g (3 eq.) of trimethylacetaldehyde was used instead of cyclohexanone. As a result, 2,6-di-t-butyl-4-piperidone and 2,2-dimethyl-6-t-butyl-4-piperidone were obtained. Oily substance was separated using silica gel column chromatography (developing solvent; hexane:ethyl acetate), thereby obtaining 260 mg of 2,6-di-t-butyl-4-piperidone (crystal obtained by recrystallization from hexane; yield: 10%; melting point: 55.4° C.) and 300 mg of oily substance of 2,2-dimethyl-6-t-butyl-4-piperidone (yield: 12%).

2,6-di-t-butyl-4-piperidone $^1$HNMR (CDCl$_3$) δ 0.90 (18H, s, CH$_3$×6), 2.05 (2H, brt, J=3), 2.35 (2H, brd, J=3), 2.42 (2H, brd, J=3).

FAB-MS m/z 212.3 ($^+$M+1)

2,2-dimethyl-6-t-butyl-4-piperidone $^1$HNMR (CDCl$_3$) δ 0.90 (9H, s, CH$_3$×3), 1.05 (3H, s, CH$_3$), 1.10 (3H, s, CH$_3$), 2.00 (1H, t, J=3.0), 2.20 (2H, brs), 2.35 (1H, d, J=3.0), 2.85 (1H, d, J=3.0, —NCH).

FAB-MS m/z 184.3 ($^+$M+1)

Example 13

Synthesis of 2-(N-acetylpiperidine-4'-spiro)-6,6-dimethylpiperidine-4-one and bis(N-acetylpiperidine-4'-spiro)-2,6-piperidine-4-one

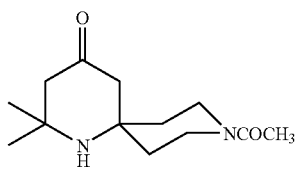

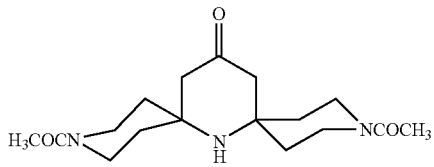

A reaction was performed in a manner similar to that in Step A of Example 2, except that 2.12 g of N-acetyl-4-piperidone was used instead of cyclohexanone. As a result, 2-(N-acetylpiperidine-4'-spiro)-6,6-dimethylpiperidine-4-one and bis(N-acetylpiperidine-4'-spiro)-2,6-piperidine-4-one were obtained. As an extraction solvent, chloroform was used. Oily substance was separated using silica gel column chromatography (developing solvent; 1 to 5% methanol: $CHCl_3$), thereby obtaining 556 mg of 2-(N-acetylpiperidine-4'-spiro)-6,6-dimethylpiperidine-4-one (crystal obtained by recrystallization from hexane-ethyl acetate; melting point: 82 to 83° C.) and 328 mg of bis(N-acetylpiperidine-4'-spiro)-2,6-piperidine-4-one (crystal obtained by recrystallization from hexane-ethyl acetate; melting point: 165 to 166° C.).

2-(N-acetylpiperidine-4'-spiro)-6,6-dimethylpiperidine-4-one

1H-NMR ($CDCl_3$) 1.18 (3H), 1.22 (3H), 1.51~1.69 (4H), 2.04 (3H), 2.71 (2H), 2.29 (2H), 3.35~3.78 (4H).
FAB-MS m/z 239.2 (+M+1)

Bis(N-acetylpiperidine-4'-spiro)-2,6-piperidine-4-one

1H-NMR ($CDCl_3$) 1.59~1.61 (8H+$H_2O$), 2.08 (6H), 2.38~2.39 (4H), 3.37~3.41 (8H).
FAB-MS m/z 322.3 (+M+1)

Example 14

Synthesis of bis(N-acetylpiperidine-4'-spiro)-2,6-piperidine-4-one-1-oxyl

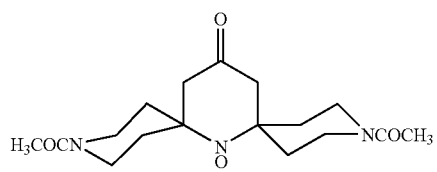

A reaction was performed in a manner similar to that in Step B of Example 1 using 110 mg of bis(N-acetylpiperidine-4'-spiro)-2,6-piperidine-4-one. As a result, 95 mg of bis(N-acetylpiperidine-4'-spiro)-2,6-piperidine-4-one-1-oxyl was obtained.
Melting point: 162 to 163° C.
FAB-MS m/z 337.3 (+M)

Example 15

Synthesis of 2-(17'β-hydroxy-17'α-methyl-5'α-androstane-3-spiro)-6,6-dimethylpiperidine-4-one and bis(17'β-hydroxy-17'α-methyl-5'α-androstane-3'-spiro)-2,6-piperidine-4-one

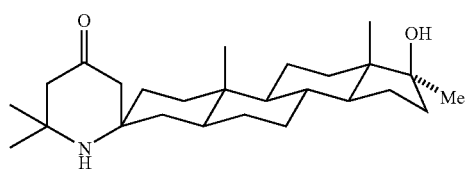

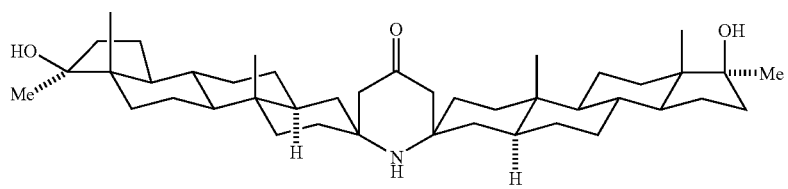

A reaction was performed in a manner similar to that in Step A of Example 2, except that 2.25 g of 17'β-hydroxy-17'α-methyl-5'α-androstane-3-one was used instead of cyclohexanone. As a result, 2-(17'β-hydroxy-17'α-methyl-5'α-androstane-3-spiro)-6,6-dimethylpiperidine-4-one and bis(17'β-hydroxy-17'α-methyl-5'α-androstane-3'-spiro)-2, 6-piperidine-4-one were obtained. As an extraction solvent, chloroform was used. Oily substance was separated using silica gel column chromatography (developing solvent; ethyl acetate:hexane), thereby obtaining 130 mg of 2-(17'β-hydroxy-17'α-methyl-5'α-androstane-3-spiro)-6,6-dimethylpiperidine-4-one (crystal obtained by recrystallization from toluene; melting point: 156.7 to 158.9° C.) and 210 mg of bis(17'β-hydroxy-17'α-methyl-5'α-androstane-3'-spiro)-2, 6-piperidine-4-one (crystal obtained by recrystallization from toluene; melting point: 292.7° C.).

2-(17'β-hydroxy-17'α-methyl-5'α-androstane-3-spiro)-6,6-dimethylpiperidine-4-one FAB-MS m/z 402.4 (+M+1)
1H-NMR ($CDCl_3$) 0.77 (Me), 0.84 (Me), 1.20 (Me), 1.20 (Me), 1.22 (Me), 2.19 (2H), 2.26 (2H)

Bis(17'β-hydroxy-17'α-methyl-5'α-androstane-3'-spiro)-2,6-piperidine-4-one

FAB-MS m/z 648.0 (+M+1)
1H-NMR ($CDCl_3$) 0.81 (Me×2), 0.83 (Me×2), 1.21 (Me×2), 2.41 (2H)

Test Example

Reactivities to Hydroxyl Radical and Reactivities to Ascorbic Acid

In order to examine reactivities of the following 3 types of TEMPO-based nitroxyl radical derivatives, in which substituents at position-2 and position-6 in one derivative are different from those in another derivative, to free radical:

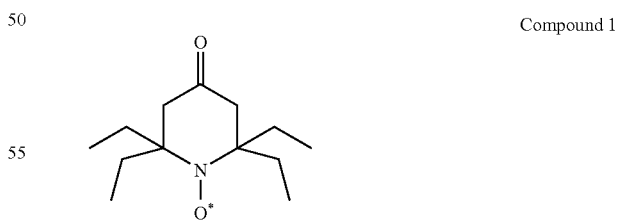

Compound 1

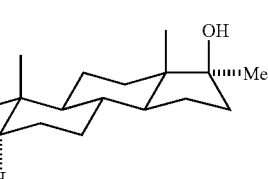

-continued

Compound 2

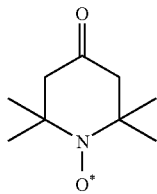

Compound 3

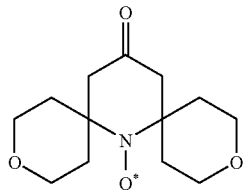

according to the method of Takeshita et al. (Biochimica et Biophysica Acta, 1573, 156-164 (2002)), the following procedure was carried out. Nitroxyl radical (25 μM) was mixed with $H_2O_2$ (10 mM), and thereafter a specific amount of the mixture was collected in a capillary and irradiated with UV (100 to 120 mW/cm$^2$) to generate OH radical. The reactivities thereof to the nitroxyl radical were examined using X-band ESR. As a result, the 3 types of nitroxyl radical derivatives exhibited the same level of reactivity to OH radical (see FIG. 1). The reactivities to hydroxyl radical were as follows: Compound 1>Compound 3>Compound 2.

Figure 2:
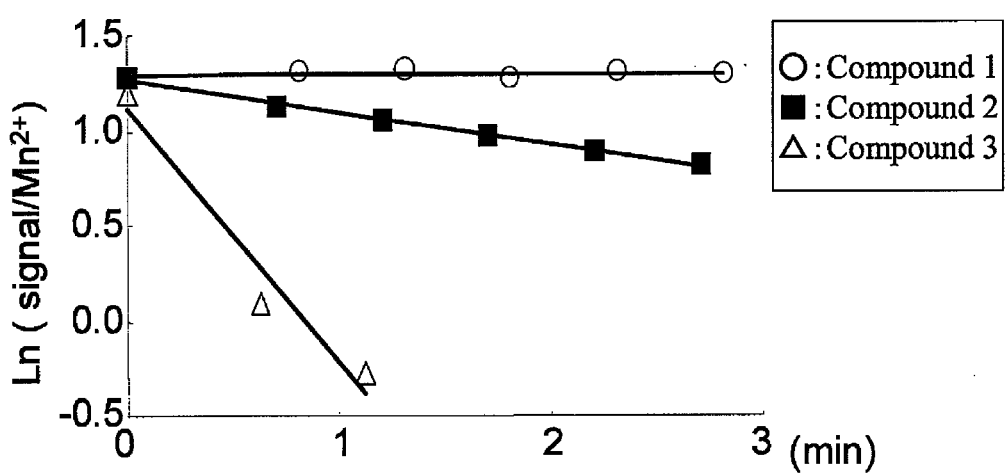
FIG. 2 is a graph for comparison between reactivities of 3 types of TEMPO-based nitroxyl radical derivatives, in which substituents at position-2 and position-6 in one derivative are different from those in another derivative, to ascorbic acid.

It has been reported that nitroxyl radical also reacts with a reduction substance (Couet, W. R., Tetrahedron, 41(7), 1165-1172 (1985); Finkelstein, E., Biochimica et Biophysica Acta, 802, 90-98 (1984)). Therefore, the following procedure was carried out. After nitroxyl radical (10 to 50 μM) was mixed with ascorbic acid (100 μM to 2 mM), a specific amount of the mixture was collected in a capillary, and thereafter the measurement was started. Using X-band ESR, decrease in ESR signal intensity was observed over time, thereby examining the reactivity to ascorbic acid, which is a typical reduction substance in the living body. As a result, it was found that tetraethyl derivative (Compound 2) almost never reacts with ascorbic acid. Meanwhile, when the reactivity of 2,6-dispiro-1',1"-dipyran-piperidone-1-oxyl (Compound 3) to ascorbic acid was examined, it was found that 2,6-dispiro-1',1"-dipyran-piperidone-1-oxyl very rapidly reacts with ascorbic acid (see FIG. 2). The reactivities of the compounds to ascorbic acid were as follows: Compound 3>Compound 2>Compound 1. The results indicate that the reactivity to OH radical or ascorbic acid is changed by changing substituents at position-2 and position-6 in the TEMPO-based compound.

The above-described results indicate that a compound in which position-2 and position-6 in the TEMPO-based compound are substituted can be easily synthesized by employing the novel synthesis pathway of the present invention. According to the production method of the present invention, it is possible to create a compound which can control the reactivity to a free radical or antioxidative substance.

INDUSTRIAL APPLICABILITY

The nitroxyl radical derivative obtained according to the present invention can be widely used as a contrast agent, an antioxidative agent, etc. as well as a cell, a polymerization agent, etc. in the field of chemical industry. In particular, the $^{15}$N-labeled compound of nitroxyl radical is useful as a contrast agent for following a free radical reaction in vivo.

The invention claimed is:

1. A method for producing a 2,6-substituted-4-piperidone derivative represented by the following formula:

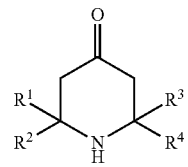

(A)

wherein in the formula: $R^1$ and $R^2$ and $R^3$ and $R^4$ are independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom, wherein the method comprises the step of reacting a triacetoneamine derivative represented by formula (1):

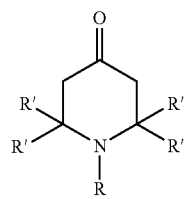

(1)

wherein in the formula: R is a hydrogen atom or a $C_1$-$C_6$ alkyl group; and the R' groups are each independently a $C_1$-$C_6$ alkyl group, with a ketone or aldehyde derivative represented by formula (2):

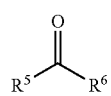

(2)

wherein in the formula: $R^5$ and $R^6$ are crosslinked to each other to form the substituted or unsubstituted $C_4$-$C_{40}$ monocyclic or polycyclic saturated ring that may be interrupted by an oxygen atom, a nitrogen atom or a sulfur atom in the presence of ammonium salt.

2. The method according to claim 1, wherein in the formula (1), R is a methyl group.

3. The method according to claim 1, wherein the 2,6-substituted-4-piperidone represented by the formula (I) and the ammonium salt are $^{15}$N-labeled compounds.

4. A method for producing a nitroxyl radical derivative represented by formula (II):

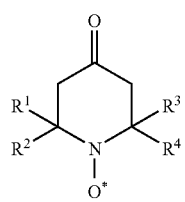

(II)

wherein in the formula: $R^1$ and $R^2$ and $R^3$ and $R^4$ are independently crosslinked to each other to form a substituted or unsubstituted $C_4$-$C_{40}$ monocyclic or polycyclic saturated ring, and the saturated ring may be interrupted by an oxygen atom, a nitrogen atom or a sulfur atom, wherein the method comprises the step of producing a nitroxyl radical by oxidizing an amino group oh a 2,6-substituted-4-piperidone derivative obtained using the method according to claim 1, which is represented by the following formula:

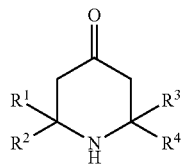

(A)

wherein in the formula: $R^1$, $R^2$, $R^3$ and $R^4$ mean the same as described above.

5. The method according to claim 4, wherein the nitroxyl radical derivative represented by the formula (II), the ammonium salt and the 2,6-substituted-4-piperidone derivative represented by the formula (I) are $^{15}N$-labeled compounds.

6. The method according to claim 1, wherein the method comprises reacting the triacetoneamine derivative represented by formula(a) with a ketone selected from the group consisting of N-acetyl-4-piperidone,

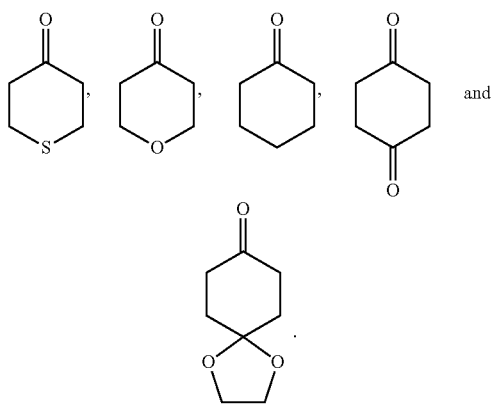

* * * * *

UNITED STATES PATENT AND TRADEMARK OFFICE
CERTIFICATE OF CORRECTION

PATENT NO. : 8,513,417 B2  Page 1 of 1
APPLICATION NO. : 12/523341
DATED : August 20, 2013
INVENTOR(S) : Hideo Utsumi et al.

It is certified that error appears in the above-identified patent and that said Letters Patent is hereby corrected as shown below:

Title Page, Item (30),

Please insert --Foreign Application Priority Data

Jan. 31, 2007 (JP) 2007022042--.

Signed and Sealed this
Twenty-sixth Day of November, 2013

Margaret A. Focarino
*Commissioner for Patents of the United States Patent and Trademark Office*